United States Patent [19]
Fox et al.

[11] Patent Number: 5,897,490
[45] Date of Patent: Apr. 27, 1999

[54] SURGICAL RETRACTION APPARATUS

[75] Inventors: William D. Fox, New Richmond; Ronald J. Kolata, Cincinnati, both of Ohio

[73] Assignee: Ethicon Endo-Surgery, Inc., Cincinnati, Ohio

[21] Appl. No.: 09/114,619

[22] Filed: Jul. 13, 1998

Related U.S. Application Data

[63] Continuation-in-part of application No. 09/012,204, Jan. 23, 1998, Pat. No. 5,846,194, which is a continuation-in-part of application No. 08/946,767, Oct. 8, 1997.

[51] Int. Cl.⁶ .................................................. A61B 17/00
[52] U.S. Cl. .......................................... 600/227; 600/232
[58] Field of Search .................................. 600/201, 210, 600/227, 228, 231, 232, 235

[56] References Cited

U.S. PATENT DOCUMENTS

| | | |
|---|---|---|
| Re. 34,150 | 12/1992 | Santilli . |
| 439,028 | 10/1890 | Washington . |
| 1,030,530 | 6/1912 | Palmer ................................ 600/227 X |
| 4,622,955 | 11/1986 | Fakhrai . |
| 4,865,019 | 9/1989 | Phillips . |
| 5,025,779 | 6/1991 | Bugge . |
| 5,109,831 | 5/1992 | Forrest . |
| 5,167,223 | 12/1992 | Koros . |
| 5,503,617 | 4/1996 | Jako ........................................ 600/201 |
| 5,520,610 | 5/1996 | Giglio .................................... 600/233 |
| 5,730,757 | 3/1998 | Benetti et al. ...................... 600/201 X |

*Primary Examiner*—Jeffrey A. Smith
*Attorney, Agent, or Firm*—Dean L. Garner

[57] ABSTRACT

In accordance with the present invention, there is provided an apparatus for pivoting a surgical retractor having two arms. The apparatus has a bridge for engaging at least one arm of the surgical retractor. The bridge has a distal end, a proximal end and a longitudinal axis extending therebetween. The bridge further includes a distal coupling attached to the distal end of the bridge for attaching the bridge to the surgical retractor. An arm extender comprising a bridge coupling and a blade is attached to the bridge and engages with the tissue of the surgical patient. The apparatus also has a lifting assembly comprising an elevator. The lifting assembly is for applying an upward force to the proximal end of the bridge, so that when the apparatus is attached to the arm of the surgical retractor, the lifting assembly pivots the retractor with respect to the surgical patient.

17 Claims, 17 Drawing Sheets

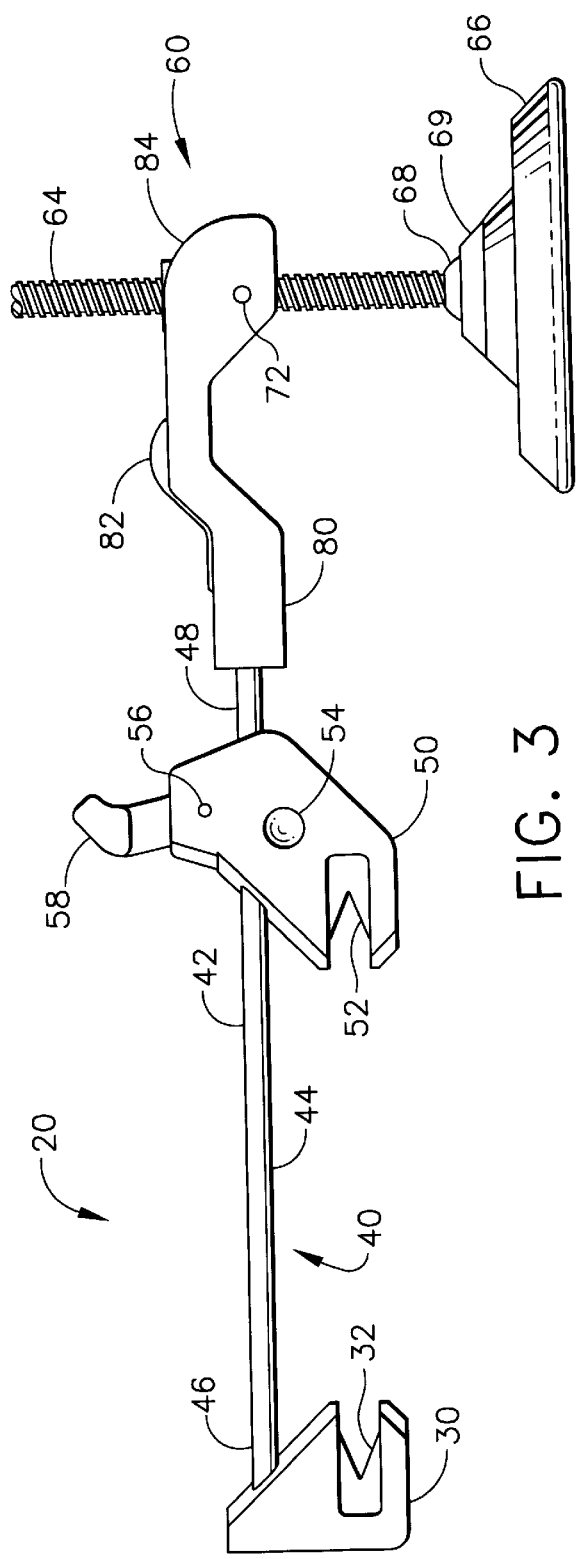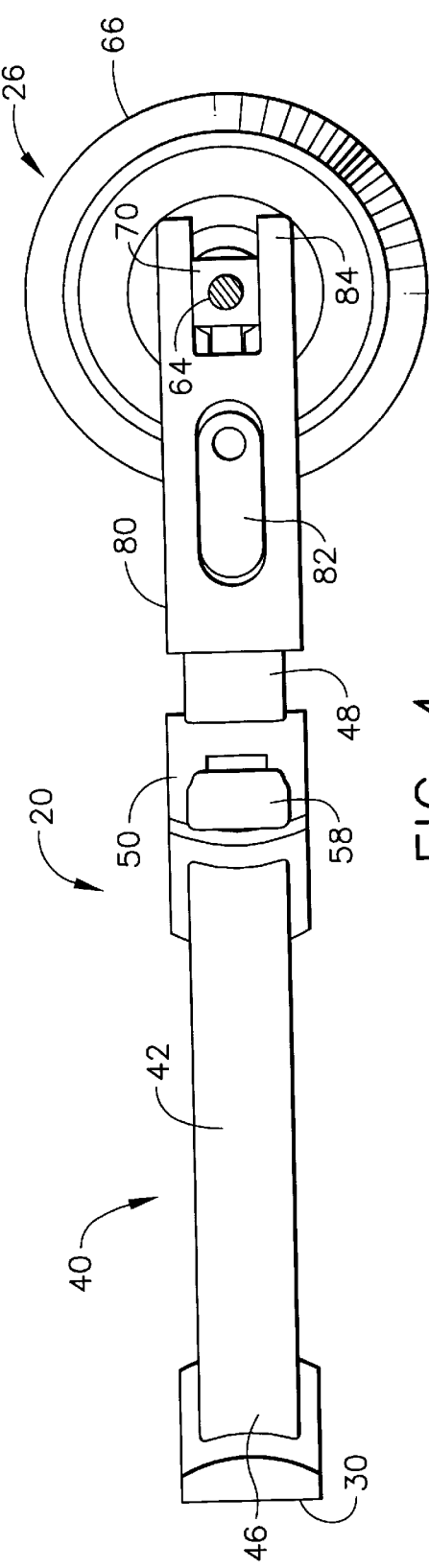

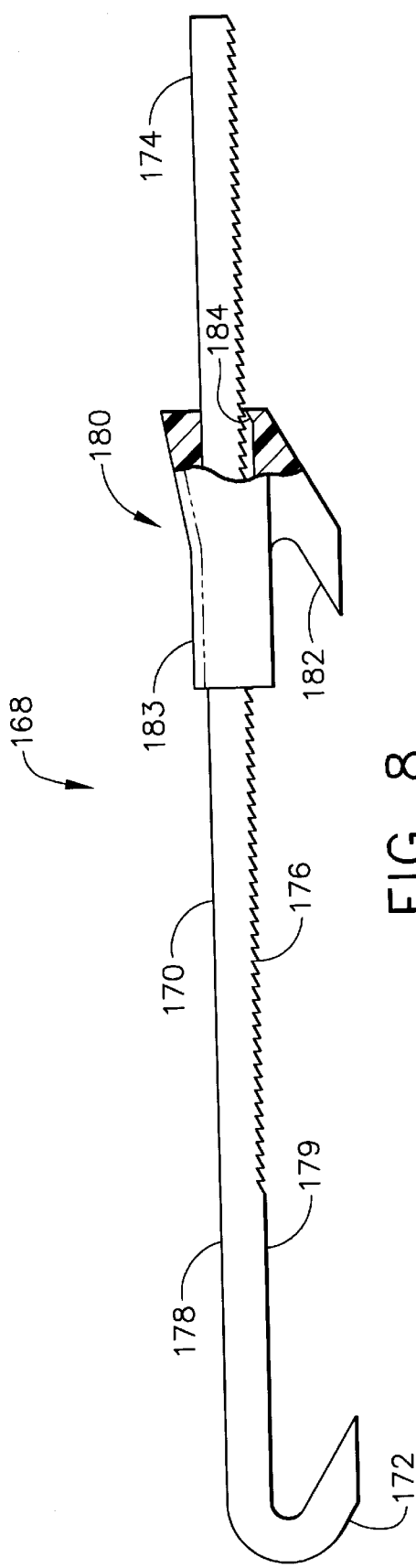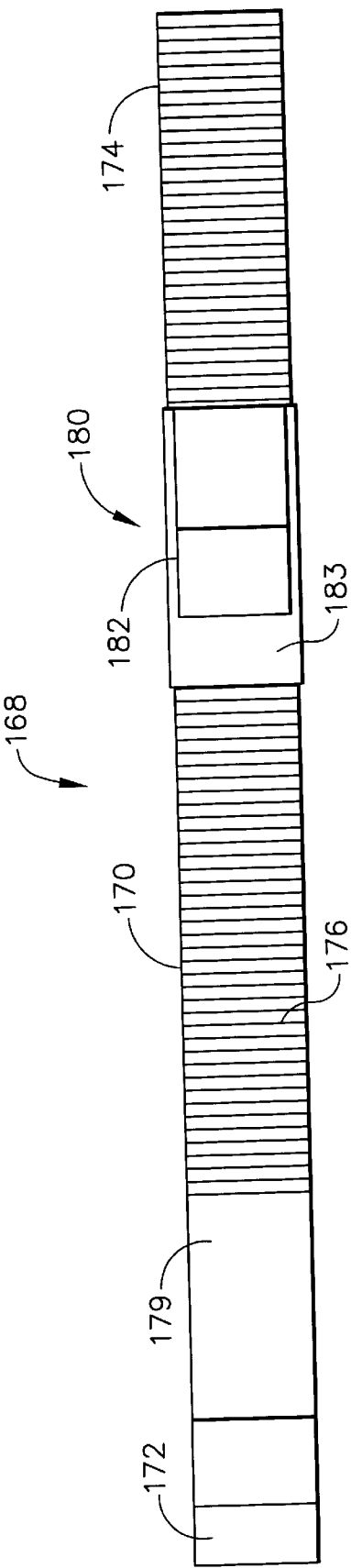

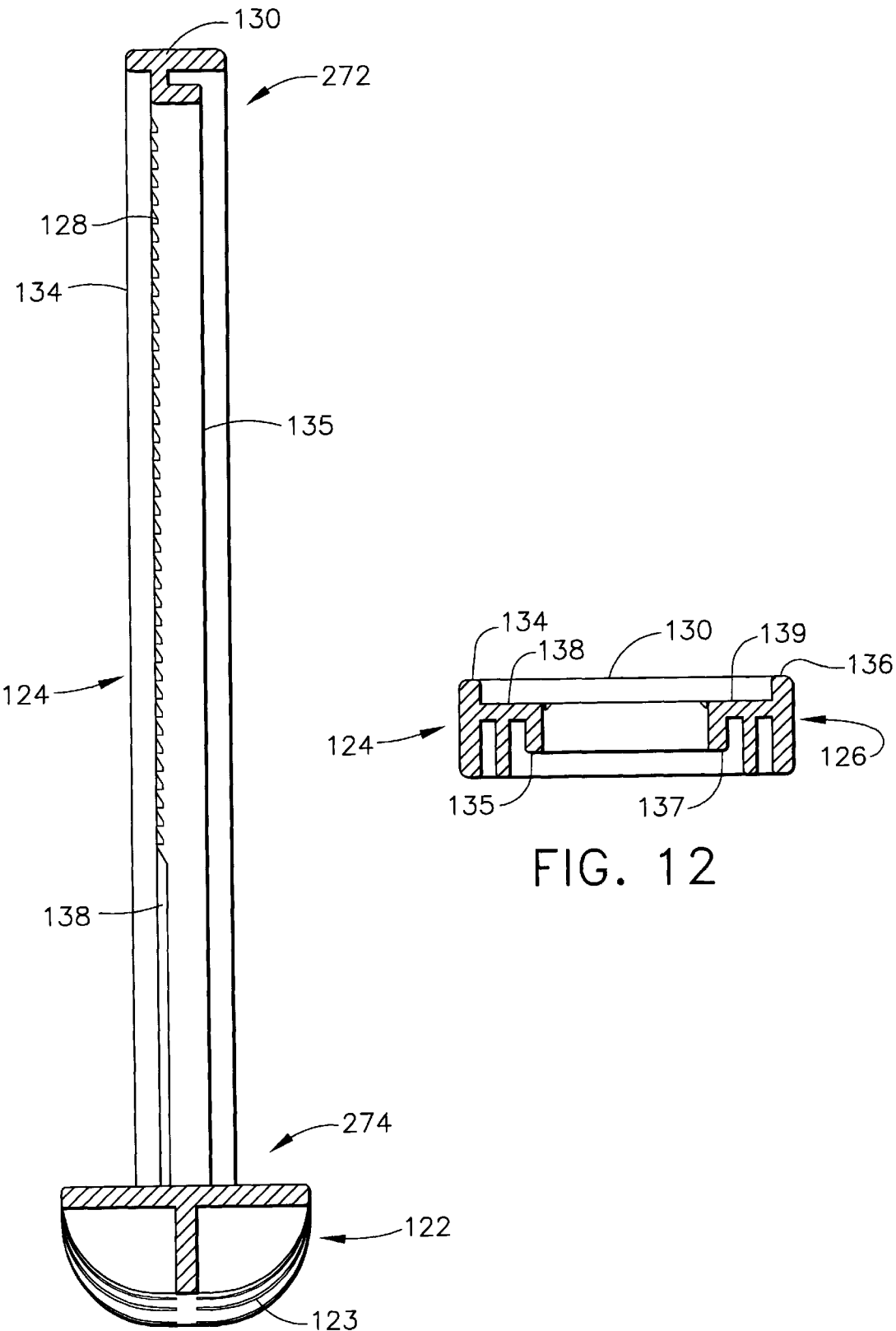

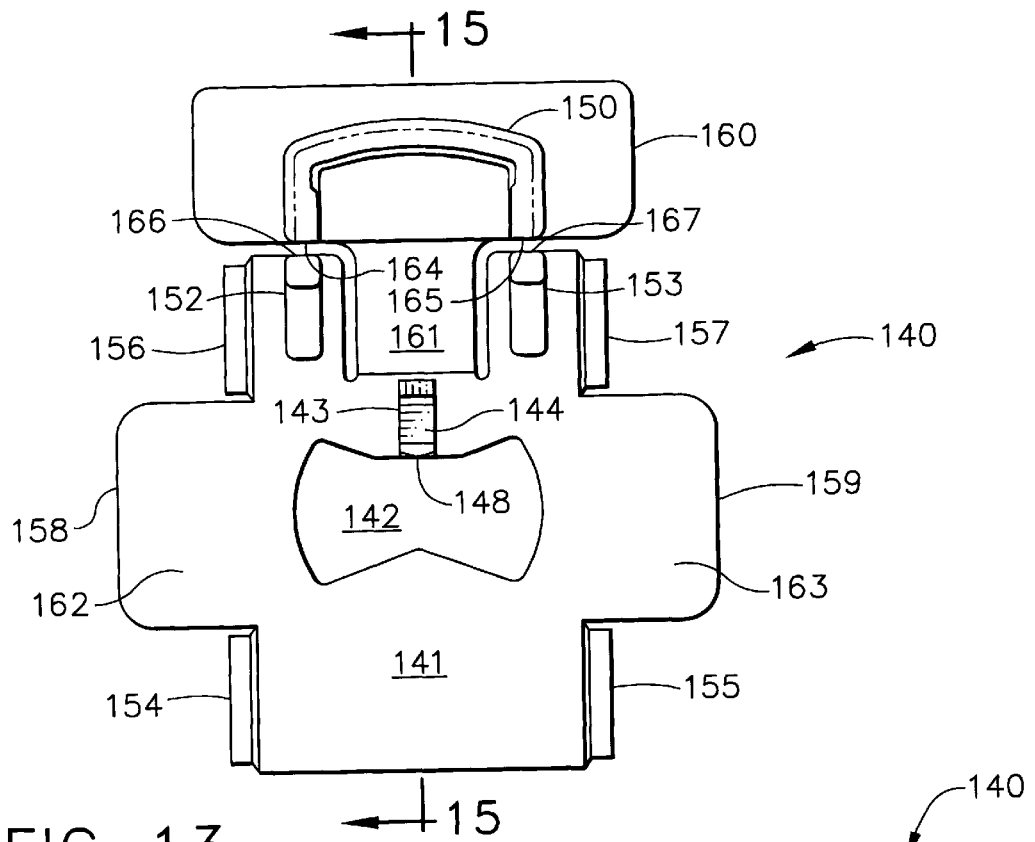
FIG. 13
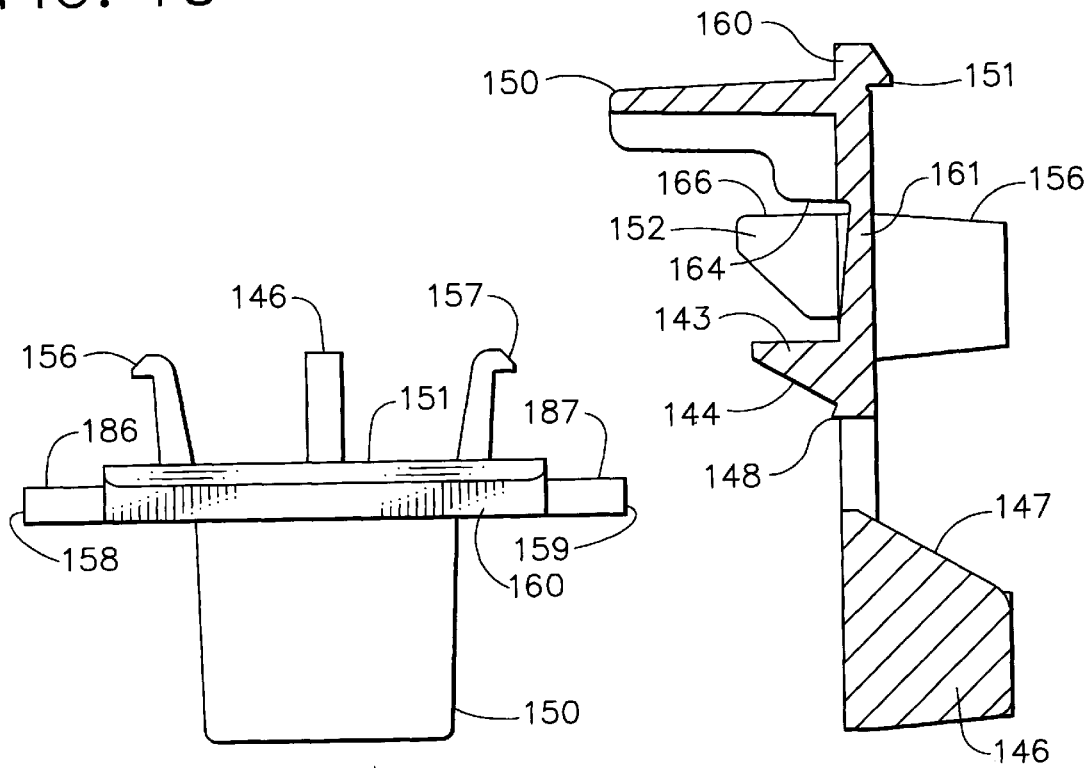
FIG. 14
FIG. 15

SURGICAL RETRACTION APPARATUS

This application is a continuation in-part of co-pending U.S. patent application Ser. No. 09/012,204 filed on Jan. 23, 1998, (now U.S. Pat. No. 5,846,194). U.S. patent application Ser. No. 09/012,204 is a continuation-in-part to co-pending U.S. patent application Ser. No. 08/946,767 (Attorney Docket No. END475) filed on Oct. 8, 1997 (pending).

FIELD OF THE INVENTION

The present invention generally relates to surgery on body tissues and organs. More specifically, the present invention relates to an apparatus for temporarily providing access to the thoracic cavity such as for the dissection and mobilization of blood vessels.

BACKGROUND OF THE INVENTION

In traditional methods for performing coronary artery bypass surgery, a segment of a blood vessel harvested from another portion of the body is used as an autogenous graft to bypass effectively the stenosed portion of the coronary artery in order to restore adequate blood flow distal to the blockage. In such a procedure, the saphenous vein is harvested from the surgical patient's leg and subsequently used as the graft vessel. In a large number of cases, the wound created in the leg is slow to heal and the patient endures considerable pain and irritation. In addition, surgeons have learned that, in general, an artery rather than a vein serves as a better, long term bypass graft when anastomosed to the coronary artery. Therefore, some surgeons harvest the radial artery from the patient's arm to be used as the bypass graft, or use both the saphenous vein and radial artery for multiple bypass surgery.

Instead of or in combination with harvesting the saphenous vein or the radial artery, many surgeons now use one of the internal mammary arteries (IMA) descending within the thoracic cavity along each side of the sternum of the rib cage. The IMA is in close proximity to the heart and therefore it is not necessary to completely remove it from the patient. The side branches are hemostatically severed, the main trunk of the vessel is occluded with a clamp, and then the IMA is severed at a point just superior to the patient's diaphragm so that the IMA is mobilized without disconnecting it from its original blood supply. The freed end of the IMA is then anastomosed to a coronary artery, usually to the left anterior descending (LAD) coronary artery, just distal to the stenosis. This procedure requires significant access and visibility into the upper thoracic cavity for the surgeon. The surgeon must free the IMA from the "ceiling" or wall of the internal thoracic cavity, while at the same time being very careful not to puncture or otherwise traumatize the IMA. The side branches of the IMA must be located and transected, usually by using an electrosurgical device, with minimal blood loss.

The most commonly used method of access to the thoracic cavity for the mobilization of the IMA and the anastomosis of it to the LAD coronary artery is a median sternotomy. For this procedure, a longitudinal incision is made through the patient's sternum on the midline of the chest. Then a surgical retractor is used to spread and hold apart the left and right rib cages, creating an opening which is typically about four to six inches wide. The muscles and other tissues of the chest wall are significantly traumatized by this procedure, and the post-operative healing process for the rejoining of the split sternum is sometimes very slow. As a result, the patient endures significant pain and the recovery time is long. In some cases there are significant complications and occasionally follow-up surgical procedures are required.

In recent years, new methods of access into the thoracic cavity have been developed in order to perform some of the surgical procedures done before through a median sternotomy. One minimally invasive method is called a mini-thoracotomy and involves access through an incision running intercostally (between two ribs) of the left chest wall. A surgical retractor again is used as for the median sternotomy, but in this case, the superior and inferior rib cages of the left chest are spread apart about two inches, thus resulting in much less overall trauma to the bones, muscles, and other tissues in the chest. Subsequently, the patient endures less pain and irritation following the surgery, and the recovery time is significantly decreased.

The mini-thoracotomy method of access to the thoracic cavity, however, has propagated the need for new surgical tools and methods because the opening into the thoracic cavity is considerably smaller than for the sternotomy. Also, since the IMA is attached to the thoracic cavity wall, the angle of approach the surgeon must use through the opening is very difficult since the inferior rib cage tends to obstruct the manipulation of surgical devices used for the procedure.

Many different surgical retractors are commercially available and are being used in thoracic surgery. There is a need for an apparatus and method that is adaptable for use with many of these surgical retractors, for the improvement of the visibility and access to the thoracic cavity. More specifically, there is a need for an apparatus to lift one side of a thoracotomic incision above the opposite side of the incision, and to do so in combination with the surgical retractor. Furthermore, there is a need for such an apparatus and method to be easy and quick to set-up since it is very important to minimize the length of time of the surgical procedure. Also, considering the high cost of surgical procedures today, it is important that such an apparatus be easy to clean and sterilize for reuse, or that it be low cost and disposable.

The apparatus also must accommodate variations in the human anatomy, specifically it should be adaptable to the curvature of the chest of the surgical patient, to the placement of the surgical incision, and to the orientation of the surgical retractor it is used with. There is a need for the apparatus to be stable during the surgical procedure, to maintain the lifting/retracting orientation desired by the surgeon, and to be as atraumatic as practical to the surgical patient.

There is a surgical need for such an apparatus which can be attached to any of numerous surgical retractors in use today, which can provide another means for support or attachment of other surgical devices used in the procedure. Often the surgeon wishes to hold or stabilize an organ or tissues within the cavity, and attach or support an ancillary holding tool on a fixed structure so that an assistant does not have to maintain the position of the holding tool throughout the procedure. Yet the surgical retractor arms may be too far away from the organ or tissue of interest to be used as a platform. What is needed is a bar or bridge that can attach to the arms of the surgical retractor and cross over the opening nearer to the organ or tissue of interest. Then this bridge can be used as a platform for supporting or attaching the ancillary holding device.

SUMMARY OF THE INVENTION

In accordance with the present invention, there is provided a device for pivoting a surgical retractor with respect to a patient it is being used on. The device has a bridge for engaging the arms of a surgical retractor. The bridge has a distal end, a proximal end and a longitudinal axis extending therebetween. The bridge further includes a distal coupling attached to the distal end of the bridge for releasably attaching the bridge to the surgical retractor. The device also has a lifting assembly comprising an elevator. The lifting assembly is for applying an upward force to the proximal end of the bridge, so that when the device is attached to a surgical retractor the lifting assembly pivots the retractor upward about the distal coupling. The elevator includes a bridge coupling for attaching the lifting assembly to the bridge, proximal to the proximal coupling. The bridge coupling has a rotatable connection for allowing the bridge to rotate about its longitudinal axis.

BRIEF DESCRIPTION OF THE DRAWINGS

FIG. 3 is a front elevational view of the rib lifting apparatus 20 depicted in FIG. 2;

FIG. 4 is a plan view of the rib lifting apparatus 20 depicted in FIG. 2;

FIG. 8 is a front elevational view of the bridge assembly 168 of the second embodiment of the present invention depicted in FIG. 7;

FIG. 9 is a bottom view of the bridge assembly 168 of the second embodiment of the present invention depicted in FIG. 7;

FIG. 11 is a sectional view taken along line 11—11 of the tower depicted in FIG. 10;

FIG. 12 is a sectional view taken along line 12—12 of the tower depicted in FIG. 10;

FIG. 13 is a front elevational view of the elevator of the second embodiment of the present invention depicted in FIG. 7;

FIG. 14 is a plan view of the elevator of the second embodiment of the present invention depicted in FIG. 7;

FIG. 15 is a sectional view taken along line 15—15 of the elevator depicted in FIG. 13;

The drawings are not necessarily to scale.

DETAILED DESCRIPTION OF THE INVENTION

Figure 1:
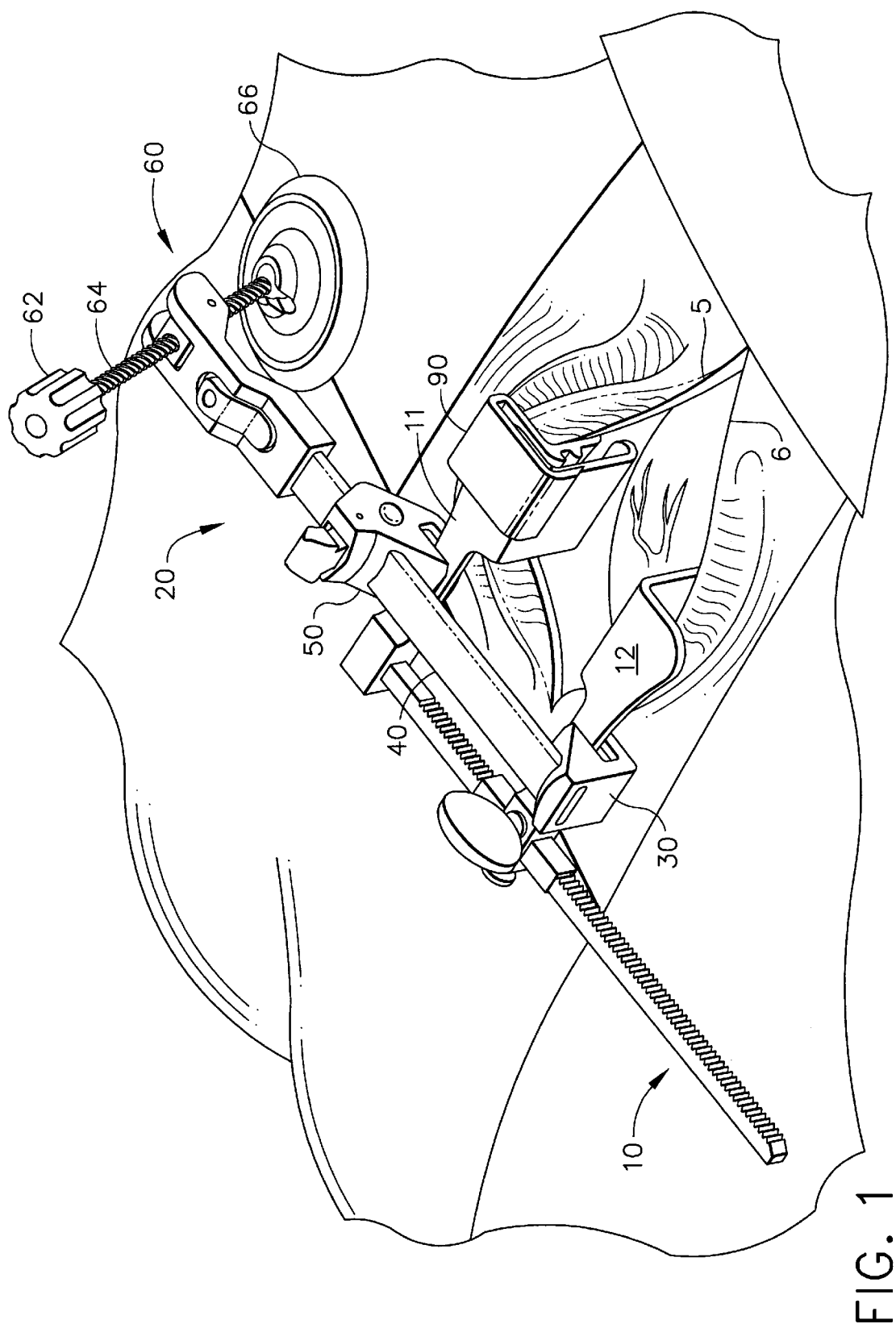
FIG. 1 is a isometric view of the first embodiment of the present invention as it is used in conjunction with a surgical retractor on a chest wall incision on a surgical patient.

The present invention described herein is comprised of two devices which can be used in conjunction with a number of commercially available, reusable, surgical retractors for improving access into the thoracic cavity. As can be seen in FIG. 1, the first embodiment of the present invention is comprised of a rib lifting apparatus 20 and an arm extender 90, both attached to a surgical retractor 10. Rib lifting apparatus 20 serves as a lever and is comprised of a distal hook 30, a bridge 40, a slideable, proximal hook 50, and a lifting sub-assembly 60. The distal hook 30 is permanently attached to the distal arm 12 of the surgical retractor 10 and serves as the fulcrum for the lever system. Bridge 40 is attached to the proximal arm 11 of the surgical retractor 10, thereby retracting the superior and inferior rib cages 5 and 6, respectively. An upward force is applied to the proximal hook 50 by the lifting subassembly 60 so that the entire system pivots upward about the distal hook 30, and thereby lifts the superior rib cage 5 above the inferior rib cage 6. It should be appreciated that the present invention could be used in the reverse manner, if the surgeon preferred, in which the inferior rib cage 6 is lifted above the superior rib cage 5. It should also be appreciated that the present invention can be used for a median sternotomy as well as the thoracotomy. In FIG. 1, the arm extender 90 is slideably attached to the proximal arm 11 of the surgical retractor 10, so that the blade 92 (see FIG. 5) is reliably supporting the superior rib cage 5 from underneath.

Still referring to FIG. 1, it can be seen that the surgical retractor shown, as for all commercially available surgical retractors of this type, has a means for mechanically adjusting the distance between the proximal and distal arms 12 and 11, respectively. Therefore it is necessary for the rib lifting apparatus 20, which is attached to surgical retractor 10, to have also a means of adjustment of the distance between the distal and proximal hooks 30 and 50, respectively. Also it can be seen that a means for adjusting the elevation of the superior rib cage 5 over the inferior rib cage 6 has been provided so that the surgeon can adjust the size of the opening into the thoracic cavity with minimal trauma to the surgical patient. Knob 62 is turned by the surgeon or an assistant to advance the screw 64 while the foot 66 bears against the chest of the surgical patient. The foot 66 is distanced somewhat superior to blade 92 (see FIG. 5) of the arm extender 90 so that an effective lifting force can be applied to the proximal hook 50 by the lifting subassembly 60.

The present invention may also be assembled to the surgical retractor 10 in the reverse manner to that shown in FIG. 1, without change to its usage or function. The physical anatomy of the surgical patient and the requirements of the surgical procedure would dictate in which direction to assemble it.

Figure 2:
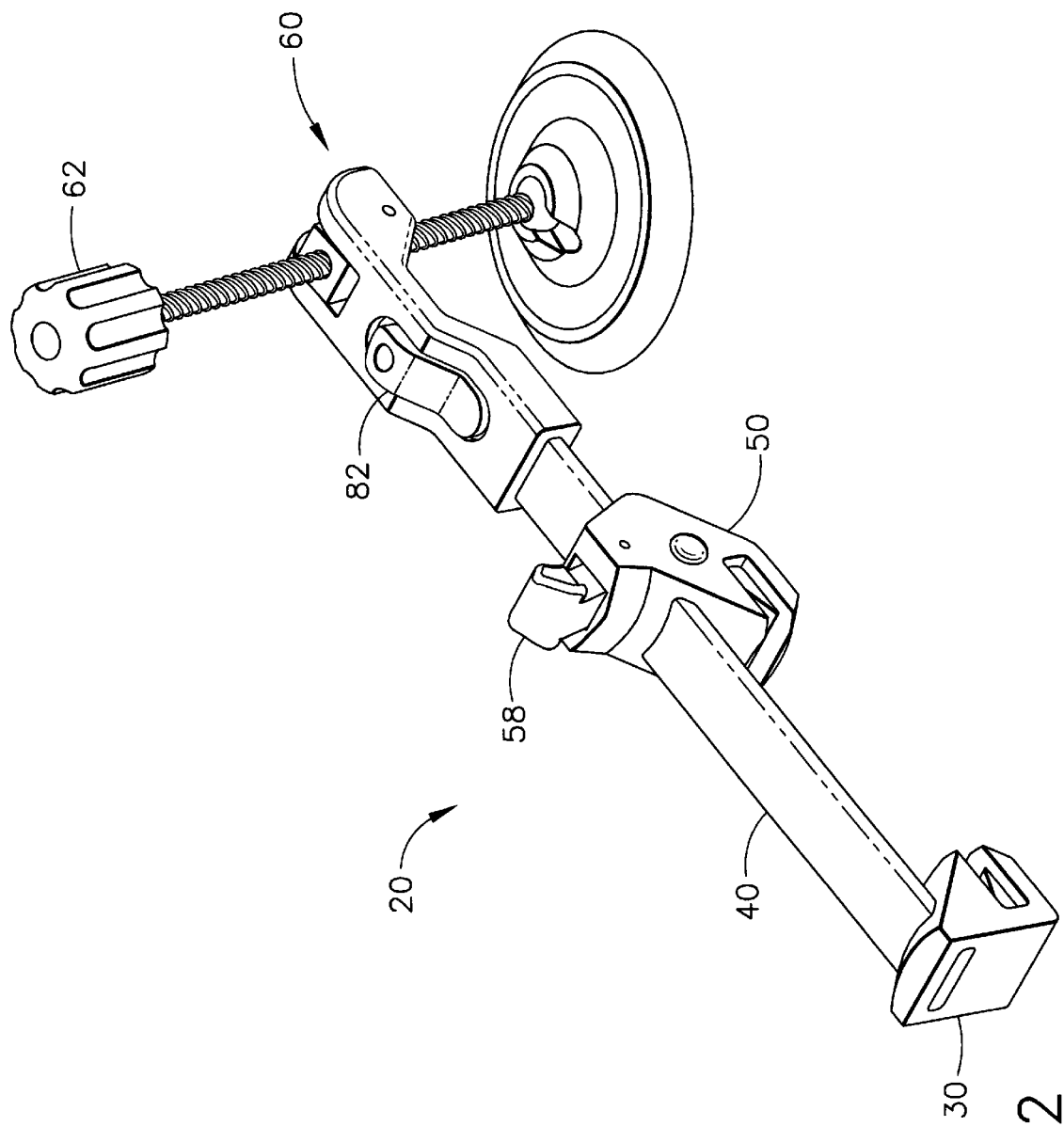
FIG. 2 is a isometric view of the rib lifting apparatus 20 of the first embodiment depicted in FIG. 1.

Turning now to FIG. 2, the rib lifting apparatus 20 is shown without the extender 90 and the surgical retractor 11 for clarity. The rib lifting apparatus has three actuators for its attachment and detachment to the surgical retractor: A slide lock lever 58 for locking the proximal hook 50 onto the bridge 40 or for unlocking it from the bridge in order to adjust the distance between the distal and proximal hooks, 30 and 50, respectively; a release button 82 for detaching the lifting subassembly 60 from the proximal end 48 of the bridge 40; and a screw knob 62 for rotating screw 64 for lifting or lowering the proximal hook 50.

FIGS. 3 and 4 are front and top views, respectively, of the rib lifting apparatus depicted in FIG. 2. Distal hook 30 may be attached to the distal end 46 of the bridge 40 by a press fit, by use of fasteners, or by a number of other means well-known to those skilled in the art. Integrally situated within distal hook 30 and spaced at a optimal distance vertically beneath the bridge 40 is V-groove 32 for the insertion of surgical retractor arm 12. Slideably mounted on the bridge 40 is proximal hook 50 which also has a V-groove 52 directly opposing the V-groove 32 on the distal hook 30. The lever 58 is raised to an up-position to allow the movement of the proximal hook 50 along the bridge 40. Indentations 54 (front and back side of proximal hook) aid the surgeon in gripping the proximal hook to position it on the surgical retractor. When the retractor arms 11 and 12 (see FIG. 1) of the surgical retractor are captured within the opposing V-grooves 32 and 52, the lever 58 is pushed down to lock the position of the proximal hook onto the bridge 40. Lever 58 pivots about lever pivot 56 and cams against the posterior surface 42 of the bridge 40, thus locking the proximal hook to the bridge.

Still referring to FIGS. 3 and 4, proximal end 48 of bridge 40 is inserted into lifting frame 80. An indentation (not visible) on bottom surface 44 on the proximal end 48 of the bridge latches with a projection (not visible) off of button 82 which is spring biased in the latching position. This attachment may be released by pressing button 82 and withdrawing the bridge 40 from the frame 80. The ability of the rib lifting apparatus to disassemble in this way is advantageous for the shipping, handling, and cleaning of the device, and also for the use of the bridge and hooks separately as will be described later for the alternate embodiment of the present invention. Integral with lifting frame 80 is lifting frame fork 84 which holds swivel block 70. The swivel block pivots about swivel pins 72, 73 (pin 72 visible only) and contains an internal screw thread for receiving screw 64. As described earlier, knob 62 is attached to screw 64. On the opposite end of the screw 64 is affixed ball 68 which in turn is captured within a cup 69 integral with foot 66. The screw is constrained by the swivel block 70 to an optimal angular variation within the plane defined by the longitudinal axis through it and the bridge 40. The range of motion for the screw 64 with respect to the foot 66 is generally conical due to the ball and cup attachment described. All of the components for the rib lifting apparatus 20 described for FIGS. 3 and 4 may be made from various metals such as stainless steel, or from various, rigid, medical grade plastics, or from a combination of metal and plastics. The device can be manufactured to be reusable or single-patient-use disposable.

Figure 5:
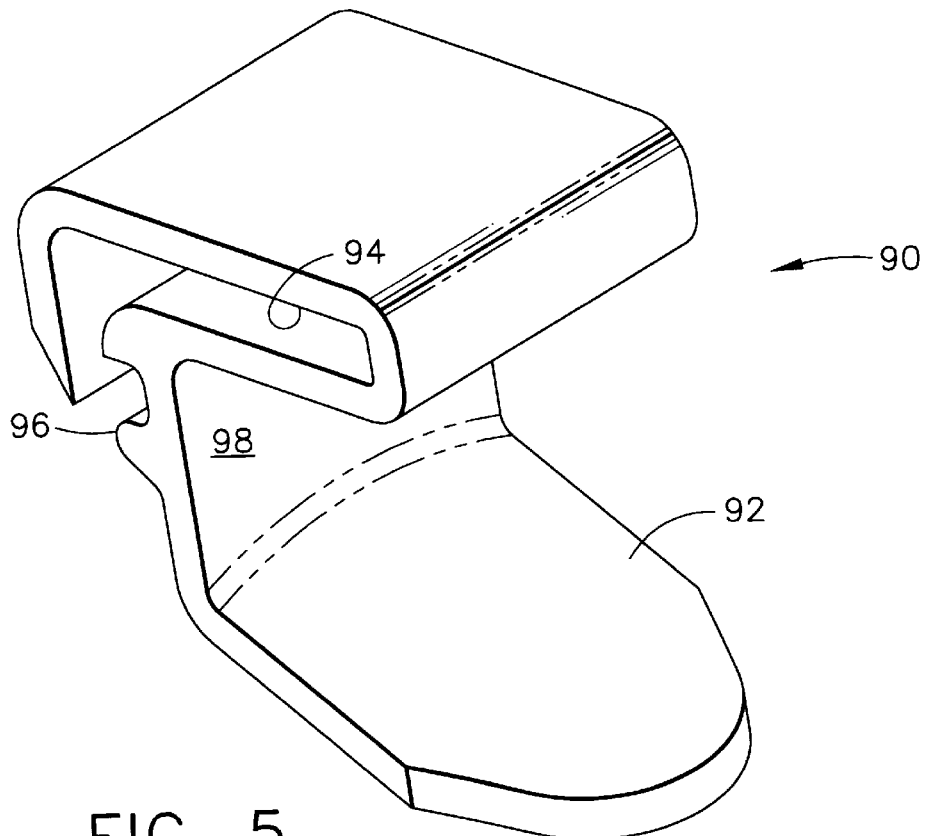
FIG. 5 is a isometric view of the arm extender 90 of the first embodiment depicted in FIG. 1.
Figure 6:
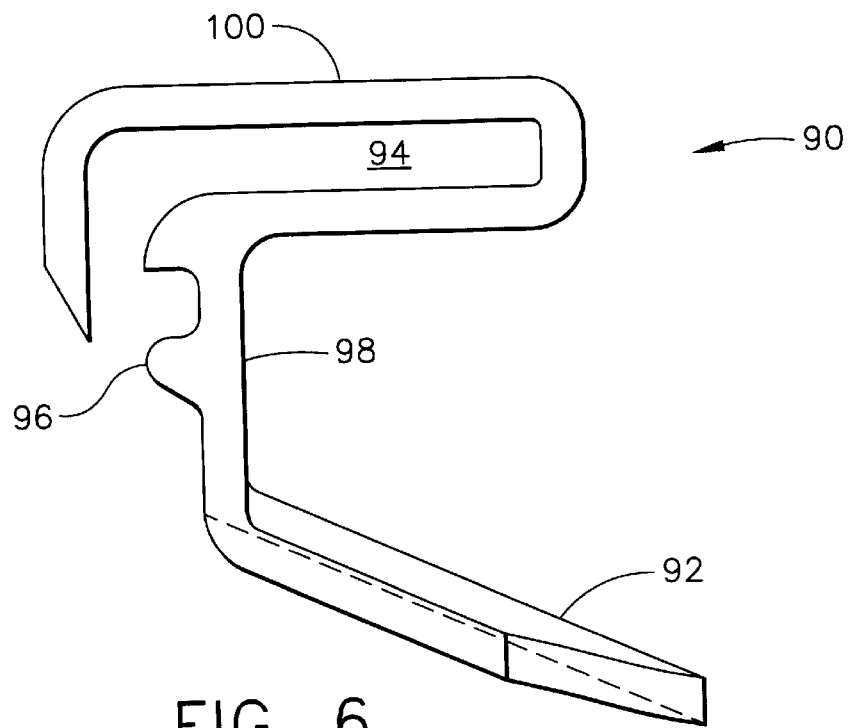
FIG. 6 is a front elevational view of the arm extender 90 of the first embodiment depicted in FIG. 1.

Now referring to FIGS. 5 and 6, the arm extender 90 is seen to consist of one piece which may be made of metal, preferably stainless steel, or of a rigid, medical grade plastic. Arm extender 90 is comprised of a blade 92, a vertical span 98, an arm wrap 100 forming an L-shape slot 94, and a fin 96. Blade 92 is designed to extend underneath the rib cage (see FIG. 1) so that an upward force can be applied by the rib lifting apparatus without the arm extender slipping off the edge of the surgical incision in the chest wall. It also distributes the lifting force over a broad area of tissue so as to minimize trauma to the delicate tissue lining the internal, thoracic cavity. Variation of the length of vertical span 98, the length of blade 92, and the angle between, is advantageous to the surgeon for accommodating variations in the surgical patients. Therefore a set of these arm extenders, each having a different geometry in these aspects, may be provided from which the surgeon may choose. The L-slot 94 is sized to fit slideably over many different sizes and kinds of commercially available, surgical retractors. The L-slot, together with the fin 96, prevent the arm extender from rotating about the arm of the surgical retractor, so as to transmit the upward force to the chest wall.

Figure 7:
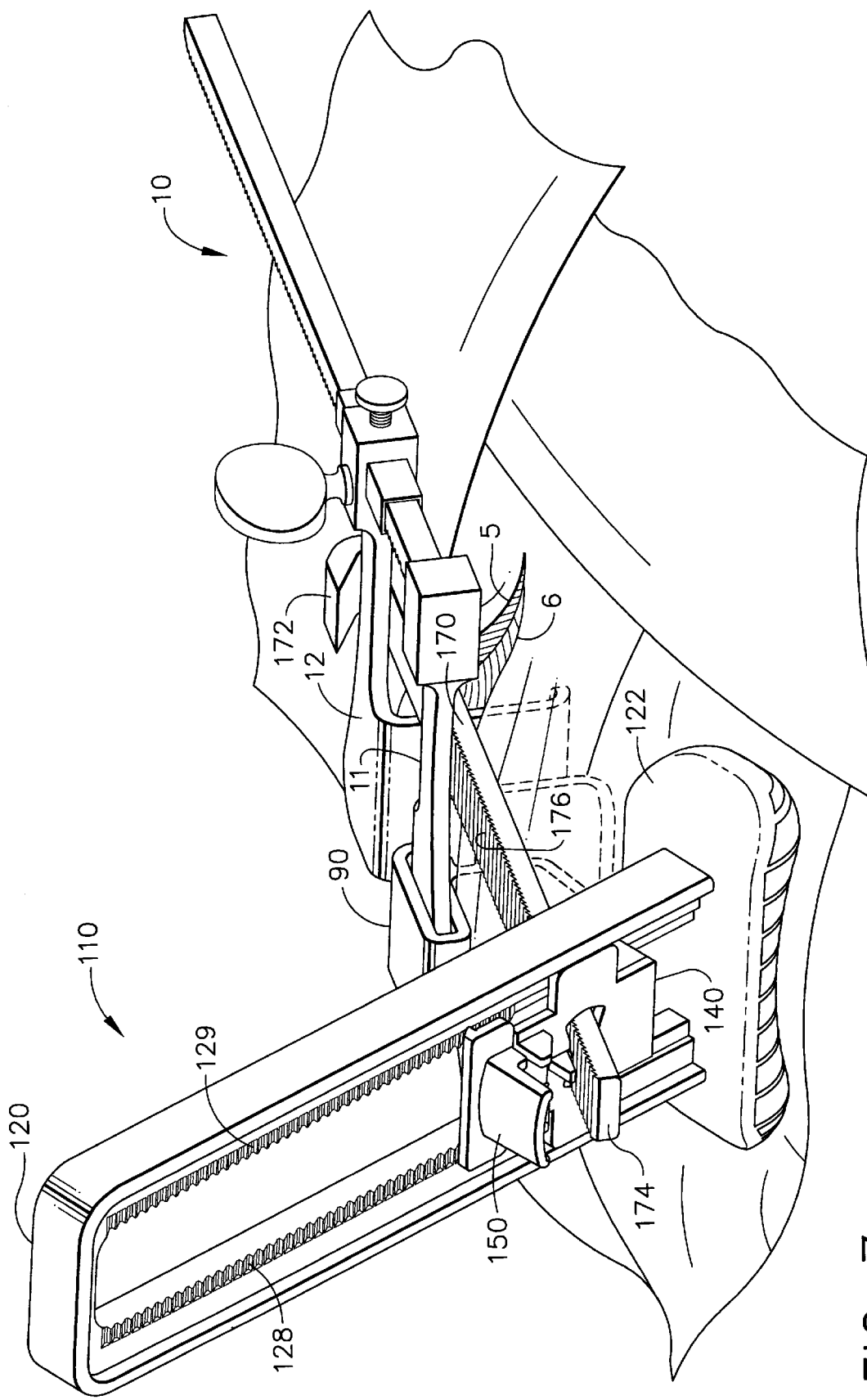
FIG. 7 is a isometric view of a second embodiment of the present invention, being used in conjunction with a surgical retractor on a surgical patient.

Referring now to FIG. 7, a second embodiment of a rib lifting apparatus 110 of the present invention is shown being used in conjunction with a surgical retractor on a surgical patient. This second embodiment 110 is much like the first embodiment in that it tilts the plane of the anatomical opening into the body cavity so that access and visibility within is enhanced. The primary difference of the second embodiment is that the same function is accomplished as before, but with fewer components. As will become apparent, the second embodiment also has a different method of assembly during the surgical procedure. The second embodiment of the present invention is the rib lifting apparatus 110 depicted in FIG. 7, comprising a bridge 170, a tower 120, an elevator 140, and an arm extender 90. Distal hook 172 of bridge 170 hooks and passes beneath retractor arm 12 of surgical retractor 10. This junction serves as the fulcrum of the lever system of the present invention. Bridge 170 passes also beneath arm 11 of the surgical retractor 10 and thus is positioned to lift the arm 11 and the superior rib cage 6 attached thereto above the inferior rib cage 5. The proximal end 174 of bridge 170 is supported within elevator 140 which in turn is adjustably mounted within tower 120. Base 122 of tower 120 bears against the chest of the surgical patient. The elevator 140 contains a locking feature to be described later which engages with ratchet teeth 176 of bridge 170 only when the tower 120 is tilted superiority with respect to the bridge 170 at an angle of approximately thirty degrees past vertical, as is shown in FIG. 7. When the tower 120 is vertical and its longitudinal axis is essentially perpendicular to the longitudinal axis of the bridge 170, then it is possible to move the tower along the length of the bridge so as to position the base 122 of the tower on the chest of the surgical patient, or to remove the tower from the bridge 170. This adjustment is easily accomplished while the elevator 140 is in the lowered position within tower 120, because the force of the bridge 170 against the retractor arm 11 is minimal. Once the base 122 of the tower 120 is properly located on the chest of the surgical patient, the elevator may be manually raised by the surgeon or surgical assistant by lifting up on the proximal end 174 of the bridge 170. A locking mechanism, to be described later, of the elevator 140 engages with the ratchet teeth 128, 129 of the tower 120 in order to maintain the vertical position of the elevator 140 during the surgical procedure. To release this lock, the release button 150 may be pushed downwardly and the elevator controllably lowers within the tower 120 due to the downward force exerted by the arm 11 of the retractor 10. At this point the tower 120 can be repositioned, and then the elevator 140 raised again, or the device may be disassembled from the surgical retractor 10.

The arm extender 90 depicted in FIG. 7 is identical in form and function to that which is depicted in FIG. 1.

Figure 16:
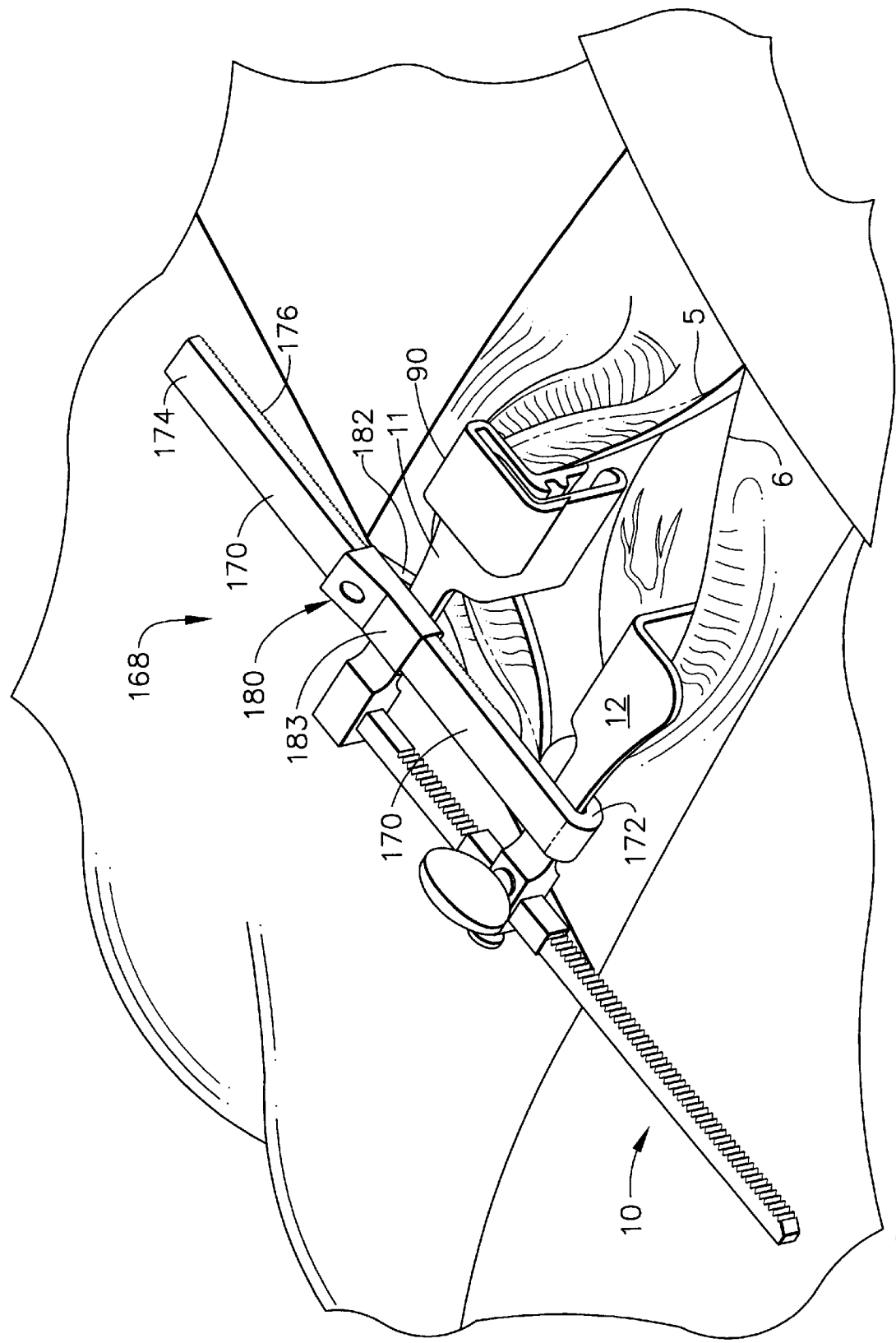
FIG. 16 is an isometric view of the bridge assembly and the arm extender of the second embodiment of the present invention being used in conjunction with a surgical retractor on a surgical patient.

FIGS. 8 and 9 show the bridge 170 depicted in FIG. 7 assembled with slide 180 (not shown in FIG. 7), hereinafter referred to as the bridge assembly 168. This arrangement provides the surgeon an option for use of a portion of the present invention as shown in FIG. 16. Specifically, the bridge assembly 168 becomes an advantageously located platform for attaching other surgical devices or simply as a support for the hand of the surgeon or surgical assistant. Here the hooks 172 and 182 of the bridge assembly 168 are facing downward towards the surgical patient and capturing the arms 12 and 11 respectively of the surgical retractor 10. Referring to FIG. 8, the bridge 170 is inserted through a rectangular, longitudinal hole in the slider frame 183. This hole is large enough to allow some angular movement of the bridge 170 within the slider 180 in the vertical, longitudinal plane. When the slider is pushed against the retractor arm 11 so that the arm presses firmly against hook 182, the slide lock pawl 184 engages the bridge ratchet teeth 176 to lock the slider in place. The same result occurs when the slider is held in place while the retractor arms 11 and 12 are spread apart slightly. The lock can easily be released by either adjusting the retractor arms to a smaller width than before, or by pressing down on the top of the slider 180 to rock the pawl 184 from engagement with the ratchet teeth 176. The bridge 170 and the slider 180 may be made of a metal such as stainless steel, or from a medical grade, rigid plastic such as a glass-filled polyetherimide. The slider 180 is not intended for use on the bridge 170 while the tower 120 is attached, although it may be if desired. The hook 172 of the bridge 170 may also be referred to as a distal coupling.

Figure 10:
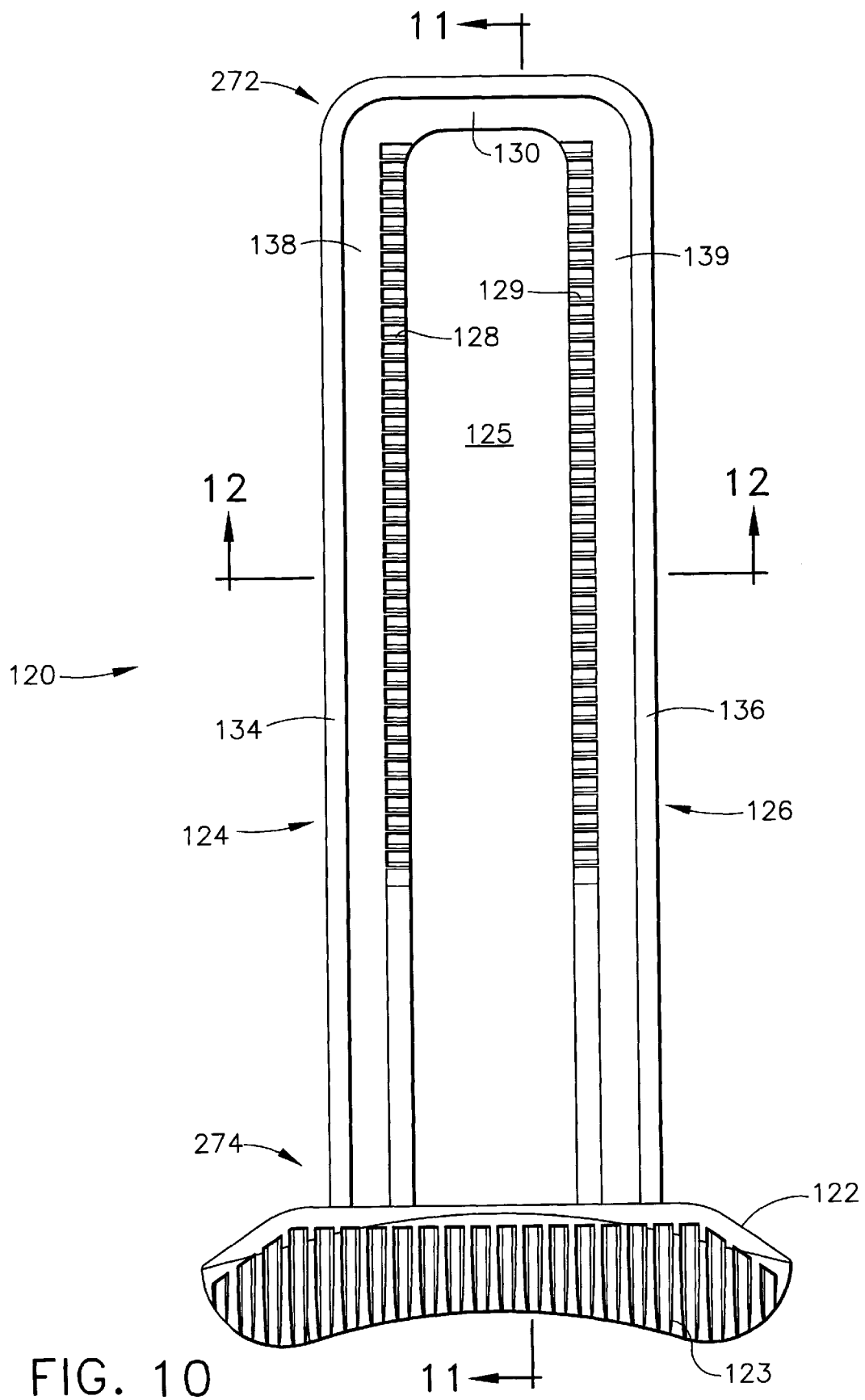
FIG. 10 is a front elevational view of the tower of the second embodiment of the present invention depicted in FIG. 7.

Next is described the features of the tower 120 and elevator 140 which work in concert to supply a upward holding force to the proximal end 174 of the bridge 170. These features can best be viewed in FIGS. 10 through 15. In FIG. 10 is a front view of the tower 120 which comprises a left column 124, a right column 126, joined at the top by cornice 130, and at the bottom by base 122. The columns 124 and 125 form an essentially rectangular opening 125. On the front of left column 124 is vertical left rail 134 which runs around cornice 130 to join vertical right rail 136 on right column 126. Also on left column 124 is a vertical array of ratchet teeth 128, and likewise on the right column are ratchet teeth 129. As can be seen in longitudinal cross section view 11—11 of FIG. 11, these teeth are designed to allow a pawl to slide freely when moving in the upward direction, but to lock in the downward direction. In FIGS. 10 and 11 the base 122 is shown to consist of a plurality of fins 123 which facilitate the injection molding of the tower 120 from a rigid, medical grade plastic such as glass-filled polyetherimide. It may also be made of a metal such as stainless steel.

FIG. 12 is lateral cross-sectional view 12—12 depicted in FIG. 10. In this view are shown left and right second rails, 135 and 137, respectively, which serve to capture the elevator 140. Rails 134 and 136 are again shown to indicate the front of the tower 120 as the top of this cross-sectional view.

The elevator 140 is shown in FIGS. 13, 14, and 15 and comprises a frame 141 (FIG. 13), extending from which is a T-beam 160, left wing 162, right wing 163, left lever stop 152, right lever stop 153, upper projection 143, lower projection 146, left lower latch 154, left upper latch 156, right lower latch 155, and right upper latch 157. Centered on frame 141 is bow tie slot 142. Extending from the front of T-beam 160 is release lever 150, and extending from the back of T-beam 160 is pawl rib 151.

The elevator 140 is slideably attached to tower 120 by the four latches, 154–157, which are flexible cantilevers. These latches are aligned and then inserted into the front of opening 125 of the tower 120. The latches snap around the edges of rails 135 and 137 of the tower (FIG. 12) so that guide edges 158 and 159 on the elevator 140 are closely interposed between rails 134 and 136 of the tower. Left and right wing surfaces 186, 187, slide against left and right sliding surfaces 138, 139, respectively, of the tower 120.

Once assembled to tower 120, pawl rib 151 can engage with left and right ratchet teeth 128, 129 of the tower to maintain the vertical position of the elevator 140. The elevator can be raised in the tower most easily by pulling up on the bridge 170 which is inserted through bow-tie slot 142. T-beam portion 161 flexes as the pawl rib 151 rides over the ratchet teeth 128, 129. To release the pawl rib from the ratchet teeth, the surgeon or surgical assistant may press down on the release button 150 and the elevator will lower to its bottom most position in the tower. Left and right stop surfaces 166, 167 of the left and right lever stops 152, 153, respectively, serve to prevent over-flexure of the T-beam portion 161 when the release button 150 is depressed.

The proximal end 174 of bridge 170 (see FIG. 8) fits loosely through bow-tie slot 142 when the longitudinal axis of the bridge 170 is normal to the plane of the elevator frame 141. The ratchet teeth 176 are to face upward when the bridge 170 is assembled with the elevator 140. (As previously noted, slide 180 of FIG. 8 is preferably not to be used with the elevator and tower.) Due to the bow-tie slot shape, the bridge is permitted to rotate slightly in both directions about its longitudinal axis. This allows the surgeon a wide range of variation in the assembly of the present invention to the surgical retractor 10, and is necessary due to the curvature of the chest of the surgical patient. As described earlier, when the tower and the elevator contained within it are tilted about 30 degrees past the perpendicular formed with the longitudinal axis of the bridge 170, the elevator becomes locked on the teeth 176 of the bridge. Bridge pawl 148 is seen in FIGS. 13 and 15 and only engages the bridge teeth 176 at the angle described. Stop surface 144 of the upper projection 143 and stop surface 147 of the lower projection 146 serve to limit the maximum amount of tilt of the elevator 140 and tower 120. The elevator 140 may be made from a metal such as stainless steel, but the preferred material is a medical grade, rigid plastic such as polyetherimide.

The second embodiment of the rib lifting apparatus 110 can be made to be reusable or single-patient-use disposable.

Figure 27:
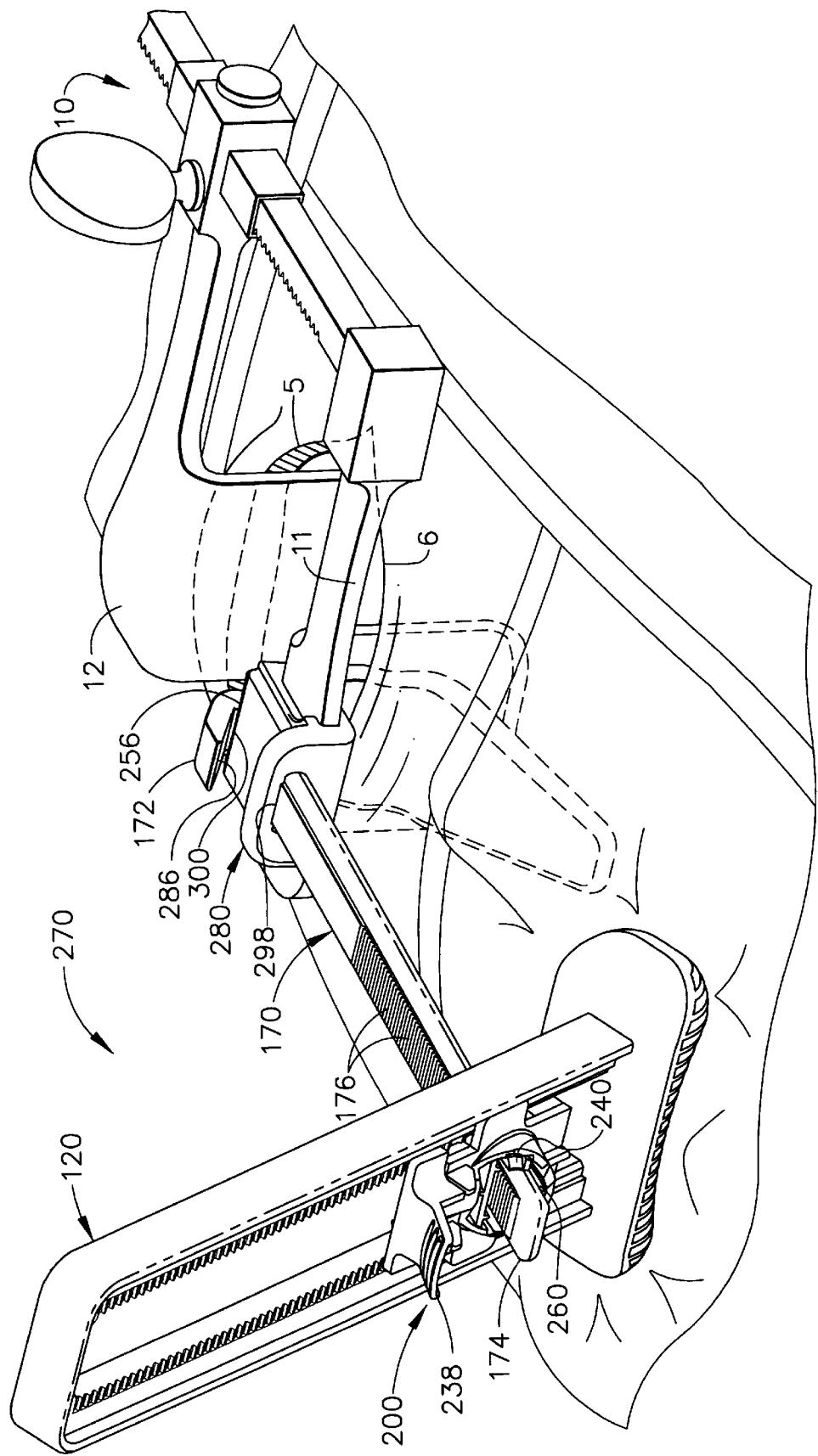
FIG. 27 is an isometric view of the third embodiment of the present invention as it is used in combination with a surgical retractor on a surgical patient.

A third embodiment of a rib lifting apparatus 270 is shown in FIG. 27. The third embodiment comprises the tower 120 and the bridge 170, both used also in the second embodiment 10. In addition, the third embodiment of rib lifting apparatus 270 comprises an elevator variation 200, a sleeve 240, and an arm extender variation 280. The rib lifting apparatus 270 is also used in combination with the conventional, surgical retractor 10. The third embodiment of the rib lifting apparatus 270 is significantly different from the second embodiment of the rib lifting apparatus 110 in that the means of attachment of the bridge to the tower 120 and to the surgical retractor 10 is different for reasons to be described.

Figure 17:
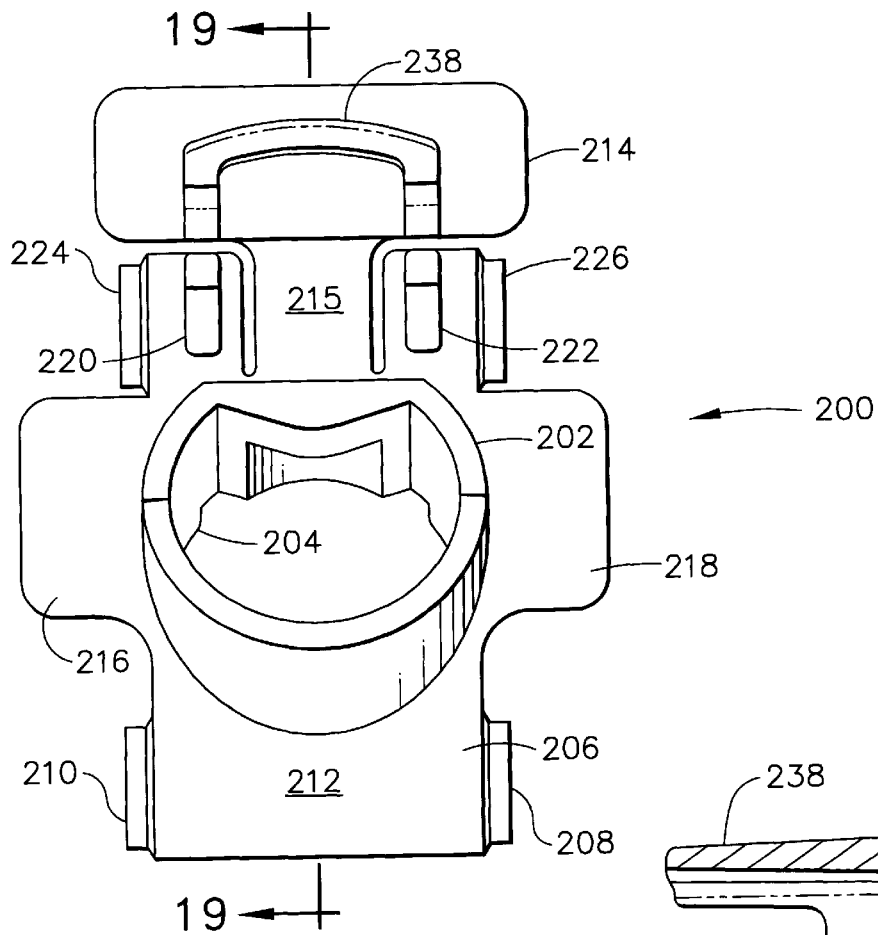
FIG. 17 is a front elevational view of an elevator variation of the third embodiment of the present invention.
Figure 19:
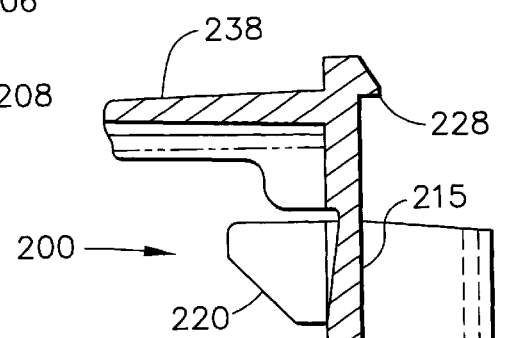
FIG. 19 is a sectional view taken along line 17—17 of the elevator variation of FIG. 17.
Figure 18:
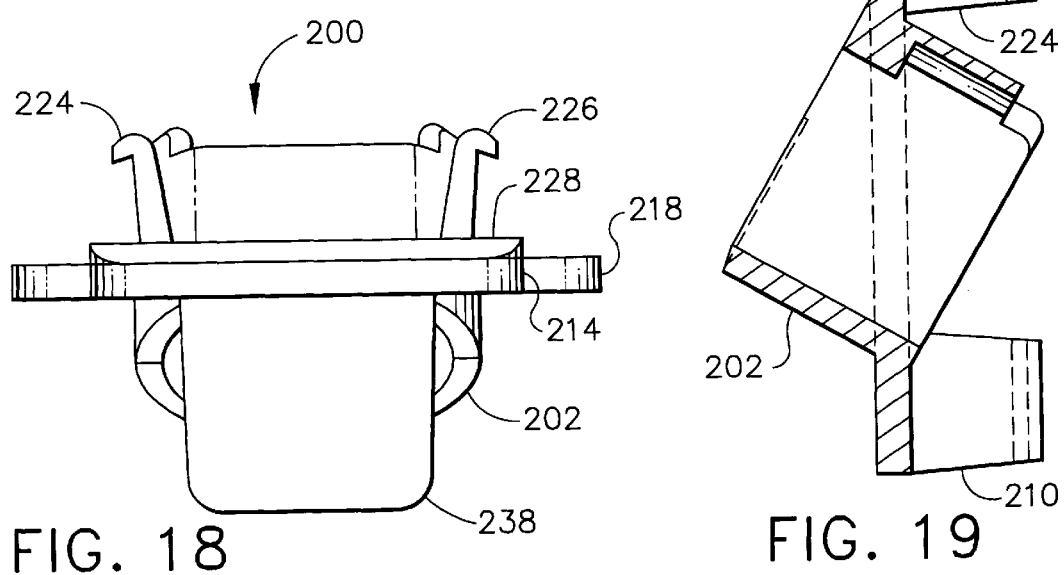
FIG. 18 is a plan view of the elevator variation of FIG. 17.
Figure 20:
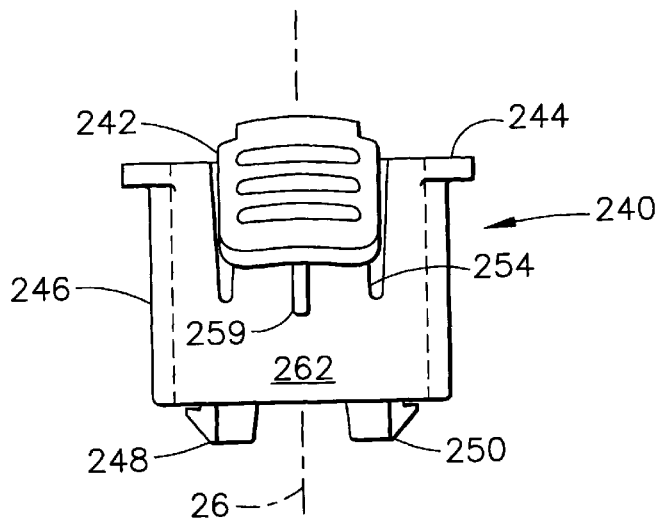
FIG. 20 is a plan view of a sleeve which is used with the elevator variation of the third embodiment.
Figure 21:
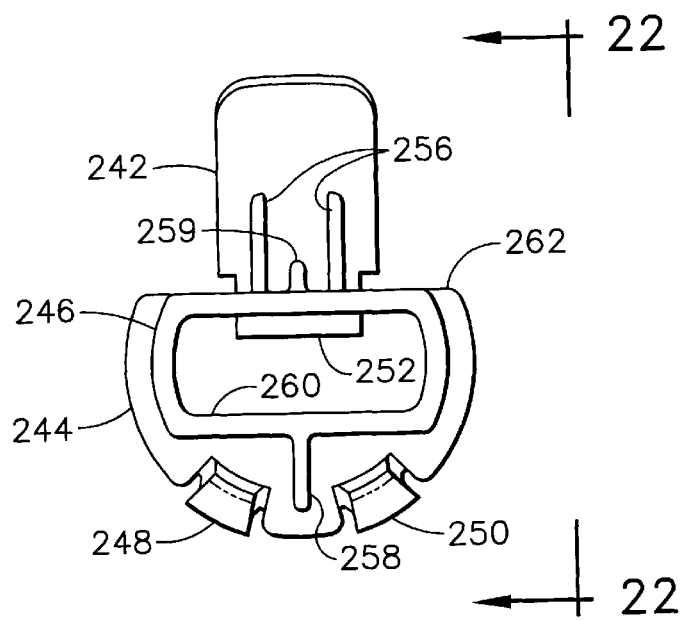
FIG. 21 is an end elevational view of the sleeve of FIG. 20.
Figure 22:
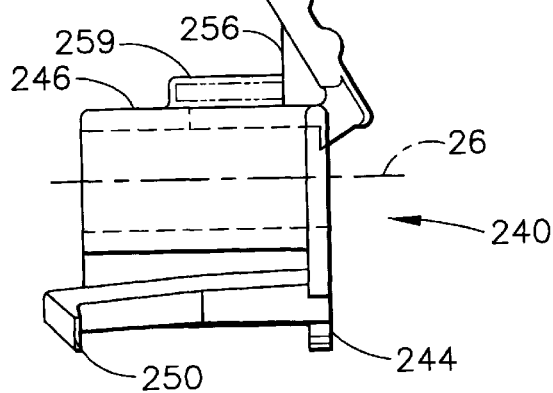
FIG. 22 is a side elevational view of the sleeve of FIG. 20.
Figure 23:
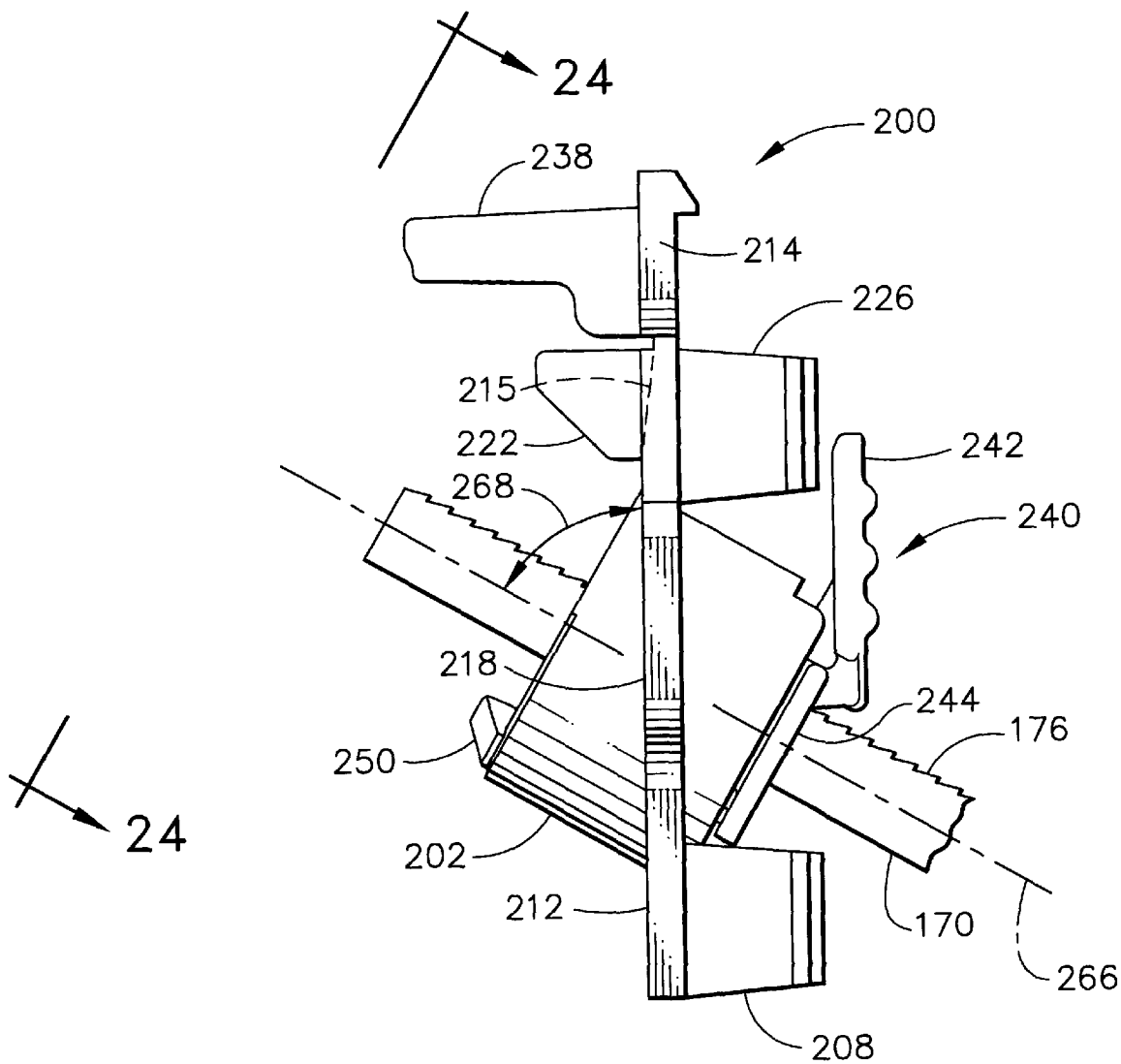
FIG. 23 is a side elevational view of the assembly of the elevator variation of FIG. 17, the sleeve of FIG. 20, and the bridge of FIG. 7.
Figure 24:
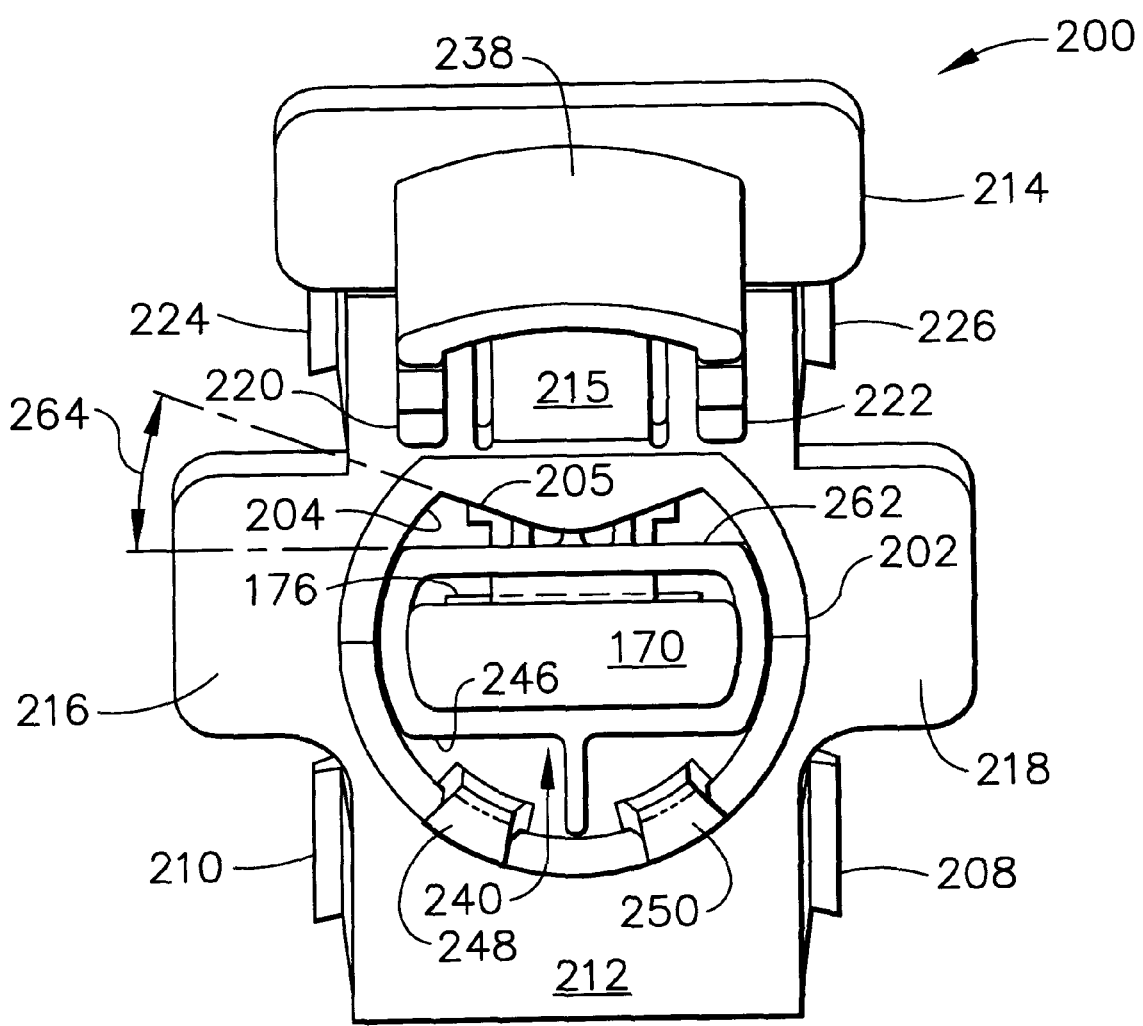
FIG. 24 is a view of the assembled elevator variation, the sleeve, and the bridge, taken from the direction of line 24—24 in FIG. 23.
Figure 25:
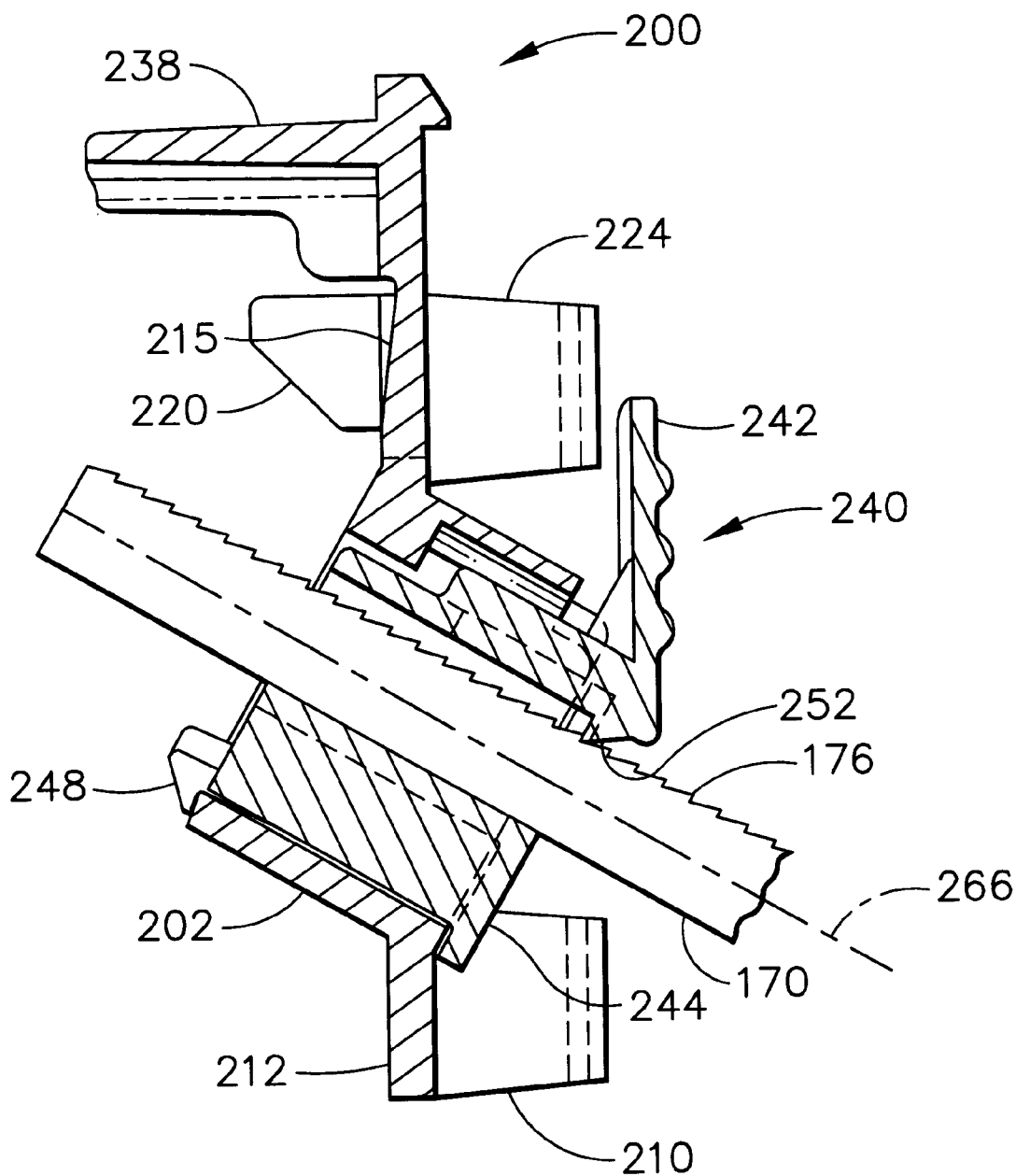
FIG. 25 is a sectional view of the assembled elevator variation, the sleeve, and the bridge shown in FIG. 23.

FIGS. 17 through 19 show an elevator variation 200 of the rib lifting apparatus 270 of the third embodiment. Elevator variation 200 is used in a manner substantially similar to the elevator 140 of the second embodiment of the rib lifting apparatus 110 shown in FIG. 7. This elevator variation 200 is used together with sleeve 240 which is shown in FIGS. 20 through 22. FIGS. 23 and 24 show the elevator variation 200, the sleeve 240, and the bridge 170 as they would be assembled in the tower 120 of FIG. 27, but with the tower 120 removed for clarity.

Referring first to FIGS. 17, 18, and 19, the elevator variation 200 comprises a frame 212, extending from which is a T-beam 214, a left wing 216, a right wing 218, a left lever stop 220, a right lever stop 222, a left lower latch 210, a right lower latch 208, a left upper latch 224, and a right upper latch 226. Projecting from front surface 206 of frame 212 is a boss 202 containing a keyed opening 204. Extending from the front of T-beam 214 is release lever 238 and from the back is a pawl rib 228. The elevator variation 200 is preferably injection molded from a rigid, medical grade plastic.

The elevator variation 200 is slidably attached to tower 120 (see FIG. 7) by the latches 208, 210, 224, and 226 in the same manner as described earlier for the elevator 140 in the description of FIGS. 13–15. Adjustment of the height of the elevator variation 200 within the tower 120 is also the same as for the elevator 140 as described for FIGS. 13–15.

Turning now to FIGS. 20–22, the sleeve 240 comprises a cannula 246 with a flange 244, a first and a second latch, 248 and 250, extending from the flange 244 and underneath the cannula 246, and a sleeve release lever 242 attached to cannula 246 by a flexible beam 254. Cannula 246 contains an essentially rectangular opening 260 for receiving bridge 170 of FIG. 7. Projecting into opening 260 is pawl 252 for engaging the teeth 176 of bridge 170. Two gussets 256 stiffen the attachment between the release lever 242 and the flexible beam 254 so that when the user presses on the release lever 242, the flexible beam 254 deflects upwardly to allow the pawl 252 to move away from the longitudinal axis 266 of FIG. 22. A top spacing rib 259 and a bottom spacing rib 258 serve to help keep the sleeve 240 centered in the keyed opening 204 of the elevator variation 200. FIG. 22 shows a partial cross section of the sleeve 240 according to view 21—21 of FIG. 21.

In FIG. 23, it can be seen how the sleeve 240 is snapped into the boss 202 of the elevator variation 200. The first and second latches, 248 (not visible in this view) and 250, retain the sleeve 240 in the boss 202. It is not necessary for the user to remove the sleeve 240 from the boss 202 during normal use of the present invention, although it is possible to do so by deflecting the first and second latches, 248 and 250, by finger pressure. In FIG. 23 the bridge 170 is shown assembled into the sleeve 240 and held at an optimal bridge angle 268 between the longitudinal axis 266 and the frame 212 of the elevator variation 200. This bridge angle 268 may vary but should be about 60 degrees as shown. The teeth 176 of the bridge 170 are engaged with the pawl 252 (see FIG. 22) to lock the bridge 170 in the longitudinal direction. By pressing the release lever 242, the longitudinal position of the bridge 170 may be adjusted, or the bridge 170 may be completely removed from the sleeve 240.

FIG. 24 shows the assembled elevator variation 200, the sleeve 240, and the bridge 170, viewed from line 24—24 of FIG. 23. Angle 264 represents the possible rotation of the bridge 170 and sleeve 240 with respect to the elevator variation 200 about the longitudinal axis 266 in both the clockwise and counterclockwise directions. This is due to the shape of the keyed opening 204 of the elevator variation 200 and the presence of key 205 which contacts top surface 262 of the sleeve 240 at the rotational limits of the bridge 170.

The sleeve 240 and the boss 202 of the elevator variation 200 essentially replace the bowtie slot 142 of the elevator 140 described earlier for the second embodiment of the rib lifting apparatus 110. The key advantage to using the elevator variation 200 with the sleeve 240 is that the means for adjusting the longitudinal position of the bridge 170 in the tower 120 is on a separate, rotationally isolated component (the sleeve 240) from the component (the elevator variation 200) containing the means for adjusting the height of the proximal end 174 of the bridge 170 within the tower 120 (see FIG. 7.) As a consequence of this arrangement, the means for fixing the longitudinal adjustment of the bridge 170 of the third embodiment of the rib lifting apparatus 270 is less likely to disengage inadvertently during use than when using the means of the second embodiment of the rib lifting apparatus 110. This is important when taking into consideration the variations of human anatomy, location of the thoracotomy, and positioning of the surgical retractor 10. These factors contribute to instability of the system. It is critical that the longitudinal adjustment of the bridge 170 be maintained so that intricate surgical procedures can be accomplished without loss of access or visibility to the surgical site.

Referring again to the third embodiment of the rib lifting apparatus 270 shown in FIG. 27, the bridge 170 is shown assembled on its distal end 172 directly to the arm extender variation 280. This arrangement has a number of advantages over the means of attaching the bridge 170 to the surgical retractor 10 shown in FIG. 7 of the second embodiment of the rib lifting apparatus 110. Firstly, the bridge 170 is no longer crossing over the incision, thereby increasing access and visibility to the surgical site. Secondly, the lifting force provided by the bridge 170 is directly in-line with the resistive force from the chest wall of the surgical patient as transmitted through the arm extender blade variation 280. This allows for a more stable system than in the second embodiment 110. Thirdly, the bridge 170 does not need to pass beneath the arms 11 and 12 of the surgical retractor 10, but rather attaches to the top of the arm extender variation 280. This arrangement makes it easier for the surgeon to set-up and adjust the present invention with the surgical retractor 10, and helps to minimize trauma to the tissues surrounding the incision.

Figure 26:
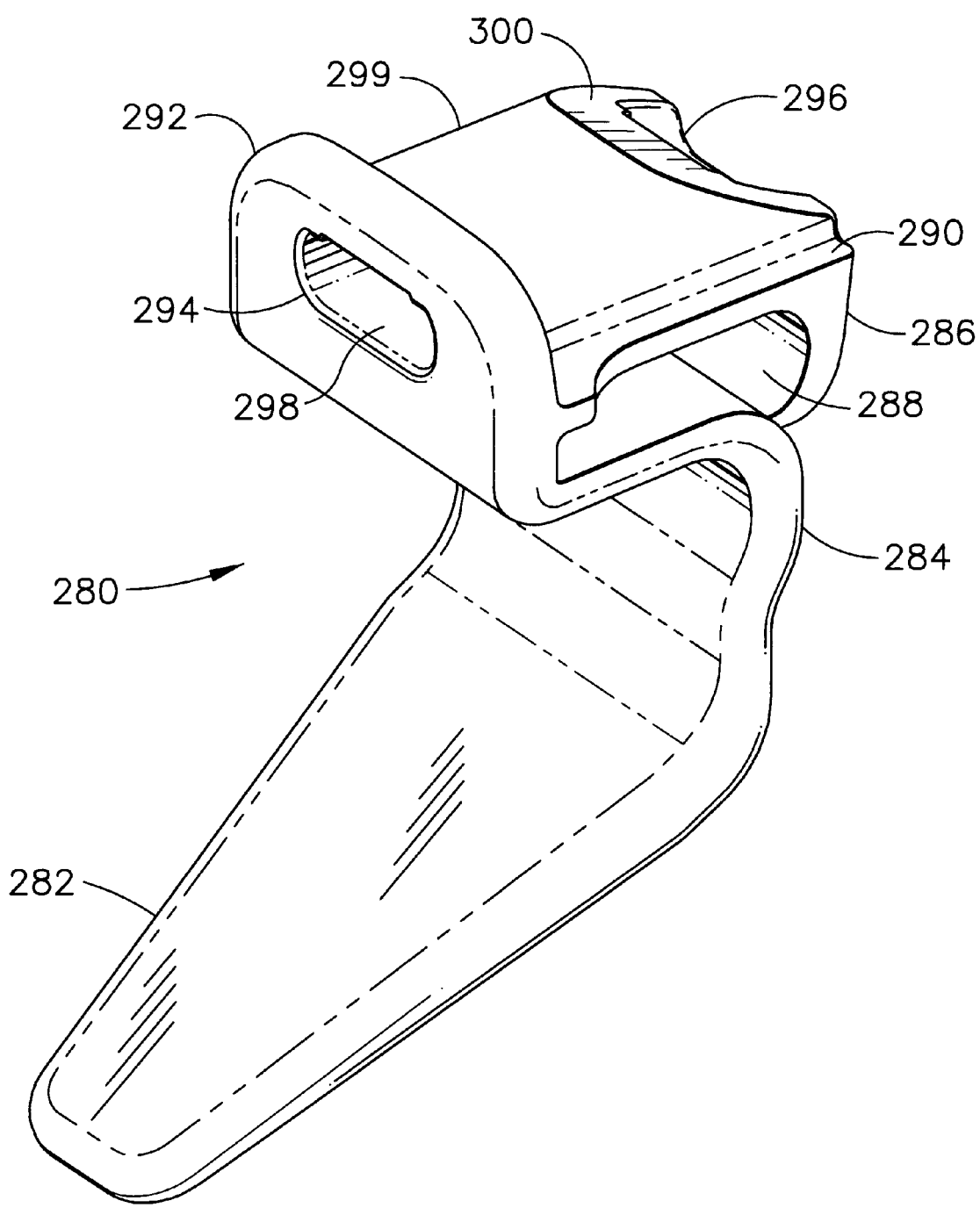
FIG. 26 is an isometric view of the arm extender variation of the third embodiment of the present invention.

FIG. 26 shows the arm extender variation 280 of the third embodiment of the rib lifting apparatus 270. The arm extender variation 280 comprises a blade 282, a vertical span 284, and a frame 286 through which extends an L-slot 288. On a top surface 290 of the frame 286 is an enclosure 299 having an opening 298 therethrough, a flange 292 on a flanged end 294, and a beveled surface 300 on beveled end 296. The arm extender variation 280 is preferably made from a medical grade, rigid plastic. The frame 286 may also be referred to as an arm coupling. The enclosure 299 may also be referred to as a bridge coupling.

As can be seen in FIG. 27, the bridge 170 is slidably inserted into beveled end 296 of the opening 298 of the arm extender variation 280, so that the teeth 176 are oriented upwards. The bridge 170 is inserted into opening 298 until the inside of hook 172 of bridge 170 abuts beveled surface 300 of the arm extender 298. The proximal end 174 of the bridge 170 may next be inserted into the opening 260 of the sleeve 240 to the desired, longitudinal adjustment. Then the elevator variation 200 may be raised to the desired elevation within the tower 120, in turn lifting the proximal end 174 of the bridge 170 and causing the surgical retractor 10 to lift the superior rib cage 6 above the inferior rib cage 5. The elevator variation 280 may be lowered by squeezing together release lever 238 and proximal end 174. The bridge 170 may be removed from the sleeve 240 by pressing sleeve release lever 242 while withdrawing the tower 120 away from the surgical site.

The arm extender variation 280 and the bridge 170 may also be manufactured as a single piece, or be manufactured as a plurality of pieces which are permanently attached together. In addition, since the present invention may be used on a plurality of physical types of surgical patients (different tissue layer thicknesses, etc.) and on a plurality of surgical retractors, it is advantageous to provide arm extender variations of a plurality of geometries. More specifically, the vertical span 284 and the blade 282 (see FIG. 26) may be provided with a plurality of combinations of length, width, and thickness. Or the L-slot 288 may be provided in a plurality of configurations to accommodate the different types of surgical retractors, although the configuration shown in FIG. 26 is designed to adapt to a wide variety of surgical retractors. The surgeon can then choose the desired arm extender variation depending on the particular physical type of surgical patient being operated on or the particular type of surgical retractor used.

The third embodiment of the rib lifting apparatus 270 can be manufactured to be single-patient-use disposable or sterilizable/reusable, depending on the selection of materials for the components.

From the foregoing, it will be observed that numerous modifications and variations can be effected without departing from the true spirit and scope of the novel concept of the present invention. It is to be understood that no limitation with respect to the specific embodiments illustrated herein is intended or should be inferred. The disclosure is intended to cover by the appended claims all such modifications as fall within the scope of the claims.

What is claimed is:

1. An apparatus for pivoting a surgical retractor with respect to a patient it is being used on, said apparatus comprising:
    a) a bridge for engaging at least one arm of a surgical retractor, said bridge having a distal end, a proximal end, and a longitudinal axis extending therebetween;
    b) a distal coupling attached to said distal end of said bridge for releaseably attaching said bridge to said surgical retractor;
    c) an arm extender comprising a bridge coupling and a blade, said bridge coupling for attaching said arm extender to said bridge, and said blade extending below and away from an arm of a retractor when attached to said bridge for engaging the tissue of the surgical patient; and
    d) a lifting assembly attached to said proximal end of said bridge, said lifting assembly including a means for applying an upward force to said proximal end of said bridge, whereby when said apparatus is attached to said surgical retractor the lifting assembly pivots said surgical retractor upward about said distal coupling.

2. The apparatus according to claim 1, whereby said arm extender is releaseably attached to said bridge.

3. The apparatus according to claim 1, wherein when said arm extender is attached to said bridge, and said blade extends below said bridge and towards the proximal end of said bridge.

4. The apparatus of claim 1, wherein said bridge coupling comprises an opening for receiving said bridge for releaseable connection thereto.

5. The apparatus of claim 1, wherein said arm extender further includes an arm coupling for attaching said arm extender to an arm of a retractor.

6. The apparatus according to claim 5, wherein said arm coupling comprises a slot for receiving an arm of a retractor for releasable connection thereto.

7. An apparatus for pivoting a surgical retractor with respect to a patient it is being used on, said apparatus comprising:
    a) a bridge for engaging at least one arm of a surgical retractor, said bridge having a distal end, a proximal end, and a longitudinal axis extending therebetween;
    b) a distal coupling attached to said distal end of said bridge for releasably attaching said bridge to said surgical retractor;
    c) an arm extender comprising a bridge coupling and a blade, said bridge coupling for attaching said arm extender to said bridge, said blade extending below and away from an arm of a retractor when attached to said bridge for engaging the tissue of the surgical patient; and
    d) a lifting assembly attached to said proximal end of said bridge, said lifting assembly comprising an elevator, whereby said elevator can apply an upward force to said proximal end of said bridge, and whereby when said apparatus is attached to said surgical retractor the lifting assembly pivots said surgical retractor upward about said distal coupling.

8. The apparatus according to claim 7, whereby said arm extender is releaseably attached to said bridge.

9. The apparatus according to claim 7, wherein when said arm extender is attached to said bridge, and said blade extends below said bridge and towards the proximal end of said bridge.

10. The apparatus of claim 7, wherein said bridge coupling comprises an opening for receiving said bridge for releaseable connection thereto.

11. The apparatus of claim 7, wherein said arm extender further includes an arm coupling for attaching said arm extender to an arm of a retractor.

12. The apparatus according to claim 11, wherein said arm coupling comprises a slot for receiving an arm of a retractor for releaseable connection thereto.

13. An apparatus for pivoting a surgical retractor with respect to a patient it is being used on, said apparatus comprising:
    a) a bridge for engaging at least one arm of a surgical retractor, said bridge having a distal end, a proximal end, and a longitudinal axis extending therebetween;
    b) a distal coupling attached to said distal end of said bridge for releaseably attaching said bridge to said surgical retractor;
    c) an arm extender comprising an arm coupling and a blade, said arm coupling for attaching said arm extender to an arm of said retractor, and said blade extending below and away from an arm of a retractor when attached to an arm of a retractor for engaging the tissue of the surgical patient; and
    d) a lifting assembly attached to said proximal end of said bridge, said lifting assembly comprising an elevator for applying an upward force to said proximal end of said bridge, whereby when said apparatus is attached to said surgical retractor the lifting assembly pivots said surgical retractor upward about said distal coupling.

14. The apparatus according to claim 13, wherein when said arm extender is attached to an arm of a retractor, said blade extends below said bridge and towards the proximal end of said bridge.

15. The apparatus of claim 13, wherein said arm coupling comprises a slot for receiving said arm for releaseable connection thereto.

16. The apparatus of claim 13, wherein said arm extender further includes an bridge coupling for attaching said arm extender to said bridge.

17. The apparatus according to claim 16, wherein said bridge coupling comprises an opening for receiving said bridge for releasable connection thereto.

* * * * *